United States Patent
Kao et al.

(10) Patent No.: US 11,164,676 B2
(45) Date of Patent: Nov. 2, 2021

(54) COMPUTER-AIDED RECOGNITION SYSTEM FOR TREATMENT RESPONSE OF RECTAL CANCER, AND COMPUTER PROGRAM PRODUCT

(71) Applicant: China Medical University Hospital, Taichung (TW)

(72) Inventors: Chia-Hung Kao, Taipei (TW); Shang-Wen Chen, Taipei (TW); Wei-Chih Shen, Taichung (TW); Kuo-Chen Wu, Taichung (TW)

(73) Assignee: CHINA MEDICAL UNIVERSITY HOSPITAL, Taichung (TW)

( * ) Notice: Subject to any disclaimer, the term of this patent is extended or adjusted under 35 U.S.C. 154(b) by 215 days.

(21) Appl. No.: 16/509,567

(22) Filed: Jul. 12, 2019

(65) Prior Publication Data
US 2020/0211712 A1 Jul. 2, 2020

(30) Foreign Application Priority Data
Dec. 28, 2018 (TW) ................ 107147715

(51) Int. Cl.
*G16H 50/50* (2018.01)
*G06N 20/20* (2019.01)

(52) U.S. Cl.
CPC ............ *G16H 50/50* (2018.01); *G06N 20/20* (2019.01)

(58) Field of Classification Search
CPC .... G06F 1/00–2221/2153; G06N 3/00–99/007
See application file for complete search history.

(56) References Cited

U.S. PATENT DOCUMENTS

| 2014/0185888 A1* | 7/2014 | Kelm | G06K 9/6282 |
| | | | 382/128 |
| 2015/0310265 A1* | 10/2015 | Suerth | G06K 9/52 |
| | | | 382/103 |
| 2020/0041510 A1* | 2/2020 | O'Toole | G16H 50/30 |

(Continued)

FOREIGN PATENT DOCUMENTS

RU 2668699 C1 * 10/2018 ............... A61B 5/00

OTHER PUBLICATIONS

Paul et al., "Feature selection for outcome prediction in oesophageal cancer using genetic algorithm and random forest classifier," Computerized Medical Imaging and Graphics, vol. 60, pp. 42-49. (Year: 2017).*

(Continued)

*Primary Examiner* — Elaine Gort
*Assistant Examiner* — Jonathon A. Szumny
(74) *Attorney, Agent, or Firm* — Bacon & Thomas, PLLC (57) ABSTRACT

A computer-aided recognition system for treatment response of rectal cancer is provided to predict the probability of a pathological complete response (pCR) of a rectal cancer patient after preoperative neoadjuvant chemoradiotherapy. The system includes a random forest model having several decision trees. Each decision tree has at least a feature node. Each feature node generates two branches according to a feature threshold, wherein each branch connects to another feature node or corresponds to an elementary pCR predicting probability. The random forest model integrates the elementary pCR probability of each decision tree, so as to generate a final pCR probability.

5 Claims, 6 Drawing Sheets

(56) References Cited

U.S. PATENT DOCUMENTS

| | | | |
|---|---|---|---|
| 2020/0069175 A1* | 3/2020 | Kumagai | A61B 3/102 |
| 2020/0082943 A1* | 3/2020 | Sakaguchi | G06N 3/08 |
| 2020/0093425 A1* | 3/2020 | Bhattacharjee | A61B 5/4818 |
| 2020/0388391 A1* | 12/2020 | Upton | G16H 50/20 |

OTHER PUBLICATIONS

Valdes et al., "MediBoost: A Patient Stratification Tool for Interpretable Decision Making in the Era of Precision Medicine," Scientific Reports, 6:37854, pp. 1-8. (Year: 2016).*

Horvat et al., "MR Imaging of Rectal Cancer: Radiomics Analysis to Assess Treatment Response after Neoadjuvant Therapy," Radiology, vol. 287, No. 3, pp. 833-843 (Year: 2018).*

Weiss et al., "Noninvasive Image Texture Analysis Differentiates K-ras Mutation from Pan-Wildtype NSCLC and is Prognostic," PLOS One, vol. 9, Issue 7, pp. 1-9 (Year: 2014).*

Mohamed et al., "Prostate cancer multi-feature analysis using trans-rectal ultrasound images," Institute of Physics Publishing, Physics in Medicine and Biology, vol. 50, pp. 175-185. (Year: 2005).*

Shi et al., "Radiomics for Response and Outcome Assessment for Non-Small Cell Lung Cancer," Technology in Cancer Research & Treatment, vol. 17, pp. 1-14. (Year: 2018).*

Blanc-Talon et al., "Advanced Concepts for Intelligent Vision Systems," 14th International Conference, ACIVS 2012 Brno, Czech Republic, Sep. 2012 Proceedings, pp. 1-540. (Year: 2012).*

Zlobec et al., "Role of tumor size in the pre-operative management of rectal cancer patients," BMC Gastroenterology, vol. 10, Edition 61, pp. 1-8. (Year: 2010).*

Xiong et al., "The Role of PET-Based Radiomic Features in Predicting Local Control of Esophageal Cancer Treated with Concurrent Chemoradiotherapy," Scientific Reports, 8:9902, pp. 1-11 (Year: 2018).*

Wei Wei et al., "Research Progress of Radiomics and its Application in Clinical of Colorectal Cancer", Chinese Journal of Biomedical Engineering, Oct. 2018, vol. 37, No. 5, pp. 513-520, English abstract.

WENWU_Both, "Machine Learning-Random Forest Algorithm", http://blog.csdn.net/wenwu_both/article, 6 pages.

Liting Shi et al., "Radiomics for Response and Outcome Assessment for Non-Small Cell Lung Cancer", Technology in Cancer Research &Treatment, 2018, vol. 17: 1-14, pp. 1-13.

* cited by examiner

COMPUTER-AIDED RECOGNITION SYSTEM FOR TREATMENT RESPONSE OF RECTAL CANCER, AND COMPUTER PROGRAM PRODUCT

CROSS REFERENCE TO RELATED APPLICATION

This application claims the benefits of the Taiwan Patent Application Serial Number 107147715, filed on Dec. 28, 2018, the subject matter of which is incorporated herein by reference.

BACKGROUND OF THE INVENTION

1. Field of the Invention

The present invention relates to the technique of computer-aided recognition and, more particularly, to the technique of computer-aided recognition for treatment response in connection with rectal cancer images.

2. Description of Related Art

Preoperative neoadjuvant chemoradiotherapy (neoadjuvant chemoradiotherapy, NCRT) followed by total mesorectal excision (TME) is the standard treatment for rectal cancer patients. Each patient may have different response to NCRT: only 15% to 27% of patients achieve a pathological complete response (pCR), 54% to 75% of patients have a partial response, and the rest of the patients exhibit no response. Patients who achieved a pCR had favorable long-term outcomes regardless of their initial stages. Therefore, predicting tumor responses to NRCT before treatment may have a considerable effect on patient management. Particularly, a "wait-and-see" policy can be suggested for patients with a pCR because surgical morbidity can be avoided. Thus far, conventional baseline images such as $^{18}$F-fluorodeoxyglucose ([$^{18}$F]FDG) positron emission tomography (FDG-PET) or magnetic resonance imaging are insufficiently accurate to select patients for organ-sparing strategies.

Therefore, there is still a need for a computer-aided recognition technique that predicts the probability of a pCR in rectal cancer patients after receiving NCRT.

SUMMARY OF THE INVENTION

One object of the present invention is to provide a computer-aided recognition technique for treatment response of rectal cancer, based on FDG-PET derived radiomics combined with random forest technique. When the training is completed, the random forest model is able to accurately predict the probability of a pCR in patients receiving NCRT.

According to one aspect of the present invention, it is provided that a computer-aided recognition system for treatment response of rectal cancer for predicting the probability of a pCR of rectal cancer patients after treatment. The system comprises a random forest model, and the random forest model comprises at least a binary decision tree model. Each binary decision tree model comprises at least a feature node. Furthermore, the feature node corresponds to a feature threshold and generates two branches according to the feature threshold, in which, each branch connects to one feature node or corresponds to an elementary pCR predicting probability. Each binary decision tree model analyzes a plurality of radiomic features of a rectal tumor image to generate the elementary pCR predicting probability, and the random forest model integrates the elementary pCR predicting probability of each binary decision tree model to generate a final pCR predicting probability.

According to another aspect of the present invention, it is provided that a computer-aided method for recognizing treatment response of rectal cancer, used to predict a probability of achieving the pCR for rectal cancer patients after NCRT, and conducted by a computer-aided recognition system for treatment response of rectal cancer, wherein the computer-aided recognition system for treatment response of rectal cancer comprises: a random forest model having at least a binary decision tree model, and each binary decision tree model comprises: a feature node corresponding to a feature threshold, and each feature node has two branches, wherein each branch connects to another feature node or corresponds to an elementary pCR predicting probability, and the method comprises steps of: analyzing a plurality of radiomic features of a rectal tumor image of the patient based on the at least a feature node through each binary decision tree model so as to generate the elementary pCR predicting probability of the patient; and integrating the elementary pCR predicting probability generated from each binary decision tree model so as to generate a final pCR predicting probability.

According to yet another aspect of the present invention, it is provided that a computer program product stored in a non-transitory computer readable medium for operating a computer-aided recognition system for treatment response of rectal cancer, and the computer program comprises: an instruction, enabling a random forest model of the computer-aided recognition system for treatment response of rectal cancer to obtain features of a rectal tumor image of the patient, wherein the random forest model comprises at least a binary decision tree model, each binary decision tree model comprises at least a feature node corresponding to a feature threshold and each feature node has two branches, wherein each branch connects to another feature node or corresponds to an elementary pCR predicting probability; an instruction, enabling the binary decision tree model of the random forest model to analyze the plurality of features based on the feature node, thereby generating the elementary pCR predicting probability of the patient; and an instruction, enabling the random forest model to integrate the elementary pCR predicting probability generated from each binary decision tree model, thereby generating a final pCR predicting probability.

Other objects, advantages, and novel features of the invention will become more apparent from the following detailed description when taken in conjunction with the accompanying drawings.

DETAILED DESCRIPTION OF THE PREFERRED EMBODIMENT

Figure 1A:
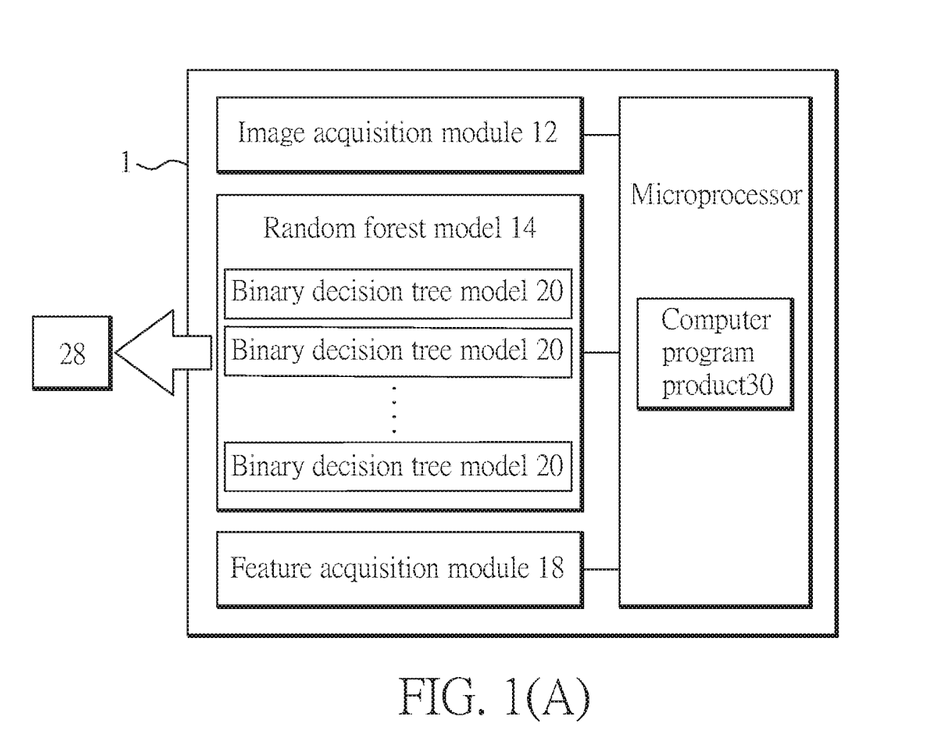
FIG. 1(A) is a schematic diagram showing the architecture of a computer-aided recognition system for treatment response of rectal cancer according to an embodiment of the present invention.
Figure 1B:
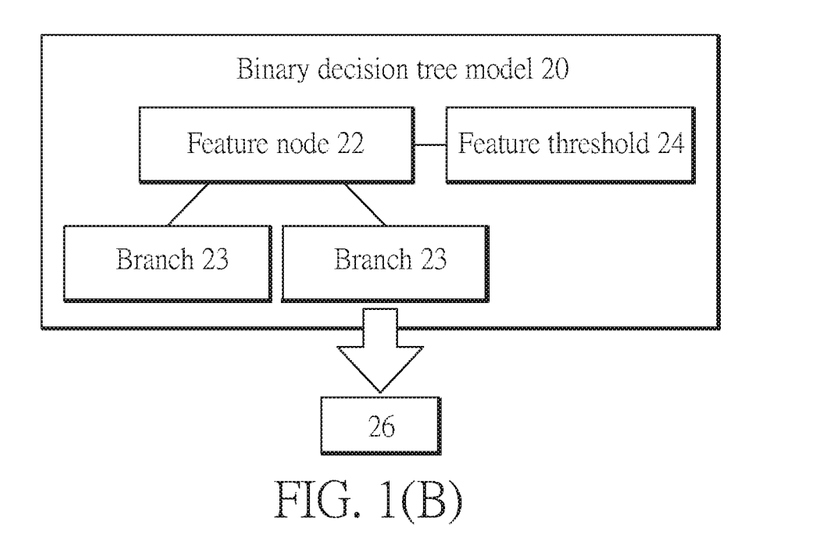
FIG. 1(B) is a schematic diagram showing the structure of a binary decision tree model of a random forest model according to an embodiment of the present invention.

FIG. 1(A) is a schematic diagram showing the architecture of a computer-aided recognition system for treatment response of rectal cancer 1 according to an embodiment of the present invention; FIG. 1(B) is a schematic diagram showing the structure of a binary decision tree model 20 of a random forest model 14 according to an embodiment of the present invention, please refer to FIGS. 1(A) and 1(B) at the same time. As shown in FIG. 1(A) the computer-aided recognition system for treatment response of rectal cancer 1 comprises a random forest model 14. In another embodiment, the computer-aided recognition system for treatment response of rectal cancer 1 may further comprise an image acquisition module 12. The image acquisition module 12 is configured to obtain image data from the outside, that is, the user (for example, a physician) may input the image data into the computer-aided recognition system for treatment response of rectal cancer 1 through the image acquisition module 12. Herein, the term "image data" may refer to a rectal tumor image of a rectal cancer patient, such as a PET/CT image of a rectal tumor, and the "image data" includes a plurality of rectal tumor image features, such as radiomic features. In one embodiment, "image data" may refer to the metabolic tumor volume (MTV) of PET images. However, the present invention is not limited thereto. For the convenience of explanation, the image data is exemplified by the MTV of PET hereinafter.

As shown in FIG. 1(B), the random forest model 14 includes at least a binary decision tree model 20, and each binary decision tree model 20 includes at least a feature node 22. Each feature node 22 corresponds to at least a feature threshold 24, and the feature node 22 has two branches 23, wherein each branch 23 may connect to another feature node 22 or correspond to an elementary pCR predicting probability 26, and at least a branch 23 may correspond to the elementary pCR predicting probability 26. When the image acquisition module 12 obtains the image data, each binary decision tree model 20 will analyze the radiomic features of the image data according to the feature threshold 24 of the feature node 22, thereby generating an elementary pCR predicting probability 26 of the patient. The random forest model 14 may integrate elementary pCR predicting probabilities 26 generated by each binary decision tree model 20 to generate a final pCR predicting probability 28. Furthermore, in one embodiment, computer-aided recognition system for treatment response of rectal cancer 1 may further comprise a feature acquisition module 18 for obtaining radiomic features from the image data. Accordingly, the computer-aided recognition system for treatment response of rectal cancer 1 predicts the probability of achieving pCR after the patient receiving the treatment (for example, NCRT).

The computer-aided recognition system for treatment response of rectal cancer 1 may be an image processing device, which may be implemented by any device having a microprocessor, such as a desktop computer, a notebook computer, a smart mobile device, a server, a cloud server or the like. In an embodiment, the computer-aided recognition system for treatment response of rectal cancer 1 may have a network communication function for transmitting data through the network, wherein the network communication may be a wired network or a wireless network, so that the computer-aided recognition system for treatment response of rectal cancer 1 may obtain image data through the Internet. In one embodiment, the computer-aided recognition system for treatment response of rectal cancer 1 may be implemented by a computer program product 30 in the microprocessor, wherein the computer program product 30 may have a plurality of instructions that enable the processor to perform particular operations, thereby enabling the processor to implement functions such as random forest model 14, binary decision tree model 20 or feature acquisition module 18. In one embodiment, the computer program product 30 may be stored in a non-transitory computer readable medium (for example, a memory). However, the present invention is not limited thereto. In one embodiment, the computer program product 30 may be pre-stored in a web server far download by the user.

In an embodiment, the image acquisition module 12 may be a physical connection port for obtaining external data. For example, the image acquisition module 12 may be a USB interface on a computer, one of various transmission line connectors and the like when the computer-aided recognition system for treatment response of rectal cancer 1 is implemented by a computer. However, the present invention is not limited thereto. In addition, the image acquisition module 12 may be integrated with a wireless communication chip, so that the data can be received through wireless transmission.

The random forest model 14 of the present invention is an artificial intelligence model for analyzing image features, which consists of binary decision tree models 20. Each binary decision tree model 20 may be trained by analyzing a large amount of image data, and build an analysis path of the features according to the radiomic features. That is, the binary decision tree model 20 can determine, by training, the feature node, the feature threshold corresponding to the feature node, and how the feature nodes are connected. The binary decision tree model 20 may be implemented by a code. In an embodiment, a preliminary model (i.e., an untrained architecture) of the binary decision tree model 20 may be pre-configured before training, such as setting the basic parameters. The computer-aided recognition system for treatment response of rectal cancer 1 enable the binary decision tree model 20 to undergo training by using the instructions in the computer program product 30, thereby building a final feature path of the decision tree model 20 (i.e., building a branch 20 of the branch 23, feature threshold 24, elementary pCR predicting probability 26 and the like). After the plurality of the binary decision tree models 20 are trained, the processor of the computer-aided recognition system for treatment response of rectal cancer 1 may integrate the binary decision tree models 20 into a random forest model 14 through the instructions in the computer program product 30. It is noted that, the untrained binary decision tree model 20 will be referred as a "preliminary model." hereinafter in order to distinguish between the pre-training and post-training binary decision tree model 20. In an embodiment, the preliminary model may undergo a training phase for training, thereby establishing a feature path, and may undergo a testing phase to test the accuracy of the feature path.

Figure 2:
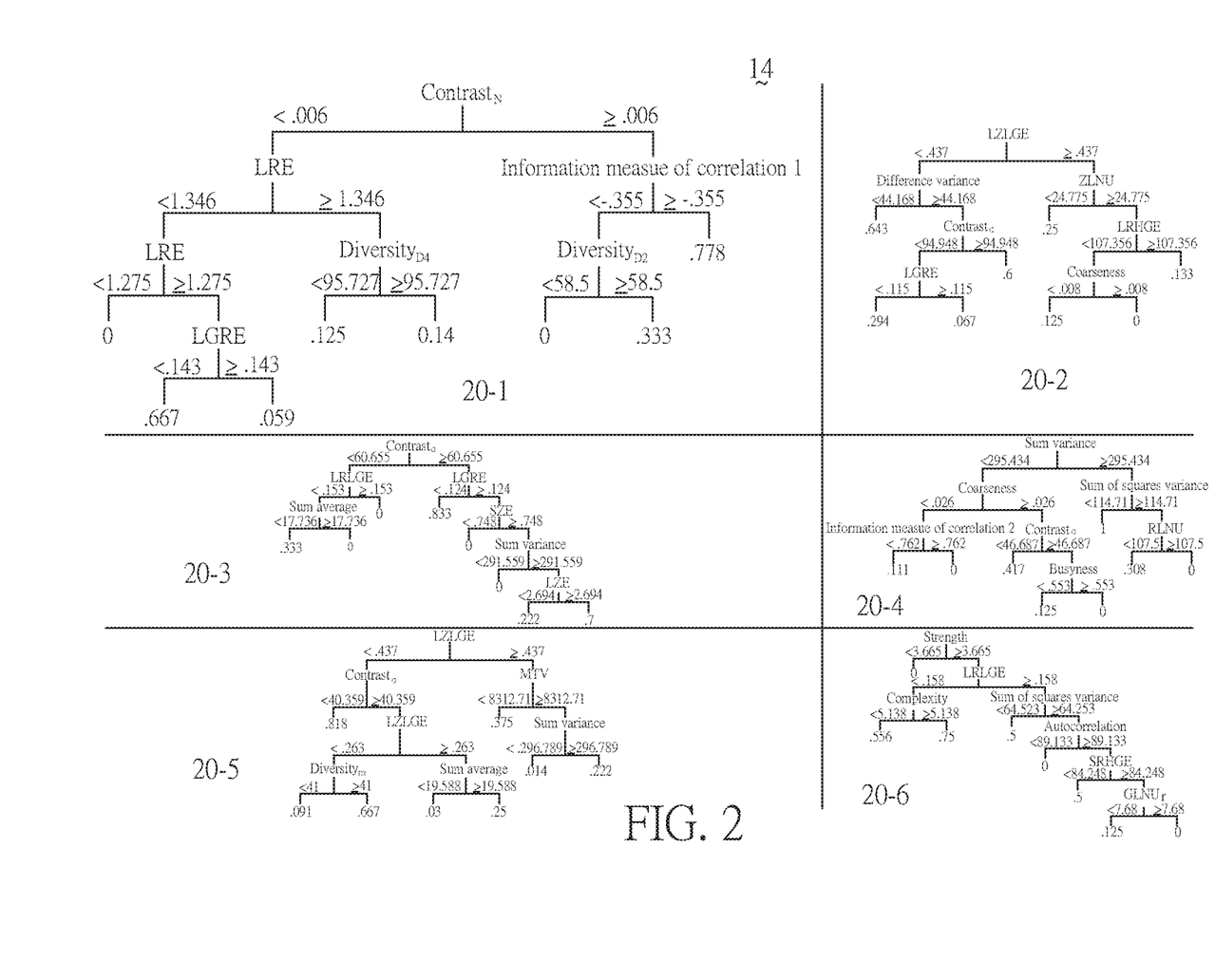
FIG. 2 is a schematic diagram showing the architecture of a random forest model according to an embodiment of the present invention.

FIG. 2 is a schematic diagram showing the architecture of a random forest model 14 (after training) according to an embodiment of the present invention. Please refer to FIGS. 1(A) and 1(B) at the same time. In order to accurately predict the pCR probability after NCRT, the number of the binary decision tree model 20 of the random forest model 14 of the present invention can be regarded as the "first variable parameter", and the number of the feature node 22 of each binary decision tree model 20 can be regarded as the "second variable parameter". The basic structure of the most suitable random forest model 14 can be found by adjusting the first variable parameter and the second variable parameter. In an embodiment, the optimal value of the first variable parameter can be regarded as a threshold (defined as a first threshold), and the first threshold is defined as when the number of the binary decision tree model 20 does not exceed the first threshold (such as less than or equal to the first threshold), the predictive power of the random forest model 14 will be increased as the number of binary decision tree models 20 increases, and when the number of the binary decision tree model 20 exceeds the first threshold (such as greater than the first threshold), the predictive power of the random forest model 14 will become moderate. In an embodiment, the optimal value of the second variable parameter can also be regarded as a threshold (defined as a second threshold), and the second threshold is defined as when the number of feature nodes does not exceed the second threshold (such as less than or equal to the second threshold), the predictive power of the random forest model 14 will be increased as the number of feature nodes of each binary decision tree model 20 increases. When the number of the feature nodes exceeds the second threshold (such as greater than the second threshold); however, the predictive power of the random forest model 14 will decline. In other words, when the first variable parameter is equal to the first threshold and the second variable parameter is equal to the second threshold, the random forest model 14 will have the predictive power with the optimal reproducibility. In the embodiment of FIG. 2, the number of feature nodes 22 in each binary decision tree model 20 is seven, and the number of binary decision tree models 20 in the random forest model 14 is six. However, the present invention is not limited thereto. As shown in FIG. 2, the random forest model 14 consists of binary decision tree models 20-1 to 20-6, wherein each of the binary decision tree models 20-1 to 20-6 has the same number of the feature nodes 22, but the content of the feature node 22, the content of the branch 23 of the feature node 22, and the feature threshold 24 corresponding to each feature node 22 may be different. In addition, the architecture of the feature path of each binary decision tree models 20-1 to 20-6 may also be different (that is, the connection manner between the feature nodes 22 may be different). The detailed description of the architecture of the binary decision tree model 20-1 is listed below, and architectures of other binary decision tree models can be inferred therefrom.

In this embodiment, the binary decision tree model 20-1 has seven feature nodes 22, each feature node represents a radiomic feature, wherein the feature nodes 22 are $Contrast_N$ feature (threshold: 0.006), LRE feature (threshold: 1.346), information measure of correlation 1 feature (threshold: −0.355), LRE feature (threshold: 1.275), $Diversity_{D4}$ feature (threshold: 95.727), $Diversity_{D2}$ feature (threshold: 58.5), and LGRE feature (threshold: 0.143). The feature threshold 24 corresponding to each feature node 22 is the threshold of the radiomic feature. Further, each feature node 22 has two branches, wherein the content of each branch may correspond to the elementary pCR predicting probability or connect to another feature node 22.

As shown in FIG. 2, the feature node is a $Contrast_N$ feature, for example. The feature threshold is 0.006, and the branches respectively are LRE feature and information measure of correlation 1, wherein the LRE feature and the information measure of correlation 1 feature are distinguished by the feature threshold of the $Contrast_N$ feature. In an embodiment, when an image data is input into the binary decision tree model 20-1, the binary decision tree model 20-1 will analyze whether the $Contrast_N$ feature in the image data is "less than 0.006" or "greater than or equal to 0.006". When the $Contrast_N$ feature in the image data is "less than 0.006", the binary decision tree model 20-1 will analyze the feature threshold of the second feature node for the image data. When the $Contrast_N$ feature in the image data is "greater than or equal to 0.006", the binary decision tree model 20-1 analyzes the feature threshold of the third feature node for the image data, and so on, the operation of the binary decision tree model 20-1 is therefore known.

As shown in FIG. 2, the feature node is $Diversity_{D4}$ feature, for example. The feature threshold is 95.727, and the branches respectively correspond to the output of "pCR predicting probability of 0.125" and the output of "pCR predicting probability is 0.14", wherein the output of "pCR predicting probability is 0.125" corresponds to "less than the feature threshold of 95.727". In an embodiment, when the binary decision tree model 20-1 uses the feature threshold of the $Diversity_{D4}$ feature to analyze the image data, if the $Diversity_{D4}$ feature in the image data is "less than 95.727", the binary decision tree model 20-1 will output the result of "pCR predicting probability is 0.125", that is, the pCR predicting probability of the patient is 1.2.5%. On the contrary, if the $Diversity_{D4}$ feature in the image data is "greater or equal to 95.727", the binary decision tree model 20-1 will output the result of "pCR predicting probability is 0.14", that is, the pCR predicting probability of the patient is 14%. Accordingly, the operation of the binary decision tree model 20-1 is therefore known.

From the above two examples, a person skilled in the art can clearly understand the operation details of the binary decision tree model 20-1, thereby inferring to the operations of other binary decision tree models.

Because of the large number of radiomic features of the PET image, some radiomic features relating to the achievement of pCR are preset as feature candidates to improve the operating efficiency of the system 1, thereby allowing the random forest model 14 to accurately predict the probability of pCR and preventing the training of binary decision tree model 20 from being too divergent. In an embodiment, a plurality of the radiomic features may be preset as feature candidates and recorded in a storage area of the system 1, the storage area may, by way of example and not limitation, be a memory. Among aforementioned feature candidates, the most suitable feature is selected, by the binary decision tree model 20, as the feature node, thereby establishing a feature path. In an embodiment, a total of 68 radiomic features are set as basic feature candidates for one PET image.

In addition, the types of radiomic features include a plurality of classical PET-related features, probability-based features, and texture features extracted from the MTV of PET images. Details of "PET related features", "probability-based features" and "texture features" will be described below.

Regarding PET-related features, in one embodiment, a classical PET-related feature may be used to describe the SUV of each voxel in the MTV or to reflect the activity of the MTV. In an embodiment, the classical PET-related feature may include: SUVmax, Mean, Median, Variance, Standard deviation, Skewness, Kurtosis, $25^{th}$ percentile, $75^{th}$ percentile, Peak, MTV, $TLG_{max}$, $TLG_{mean}$, $TLG_{peak}$, and a combination thereof. However, the present invention is not limited thereto.

Regarding the probability-based features, in one embodiment, the SUV of each voxel in the MTV are discretized using a fixed bin width of 0.001 g/ml. After the discretization, the occurrence probability of each SUV will be calculated, and the entropy, energy and/or diversity are derived therefrom. In an embodiment probability-based features may comprise: Entropy, Energy, $Diversity_{D2}$, $Diversity_{D3}$, and $Diversity_{D4}$. However, the present invention is not limited thereto.

Regarding the texture feature, in one embodiment, the SUV of each voxel in the MTV are discretized using a fixed bin number of 20 in order to calculate the texture feature. In an embodiment, the texture feature may comprise four main texture features, namely, GLCM (Gray-level co-occurrence matrix), NGLDM (Neighboring gray-level dependence matrix), GRLLM (Gray-level run-length matrix), and GLSZM (Gray-level size zone matrix). Aforementioned main texture features can be used to describe the heterogeneity of SUVs in the MTV. Furthermore, in an embodiment, the GLCM may comprise following features: Autocorrelation, $Contrast_G$, Correlation, Cluster prominence, Cluster shade, Dissimilarity, Energy, Entropy, $Homogeneity_m$, $Homogeneity_p$, Maximum probability, Sum of squares variance, Sum average, Sum variance, Sum entropy, Difference variance, Difference entropy, Information measure of correlation 1, Information measure of correlation 2, inverse difference normalized and Inverse difference moment normalized. However, the present invention is not limited thereto. In an embodiment, the NGLDM may comprise following features: Coarseness, $Contrast_N$, Busyness, Complexity, and Strength. However, the present invention is not limited thereto. In an embodiment, the GRLLM may comprise following features: SRE (short-run emphasis), LRE (long-run emphasis), $GLNU_r$ (gray-level nonuniformity for run), RP (run percentage), RLNU (run-length nonuniformity), LGRE (low gray-level run emphasis), HGRE (high gray-level run emphasis), SRLGE (short-run low gray-level emphasis), SRHGE (short-run high gray-level emphasis), LRLGE (long-run low gray-level emphasis), and LRHGE (long-run high gray-level emphasis). However, the present invention is not limited thereto. In one embodiment, GLSZM may comprise following features: SZE (short-zone emphasis), LZE (long-zone emphasis), $GLNU_Z$ (gray-level nonuniformity for zone), ZP (zone percentage), ZLNU (zone length nonuniformity), LGZE (low gray-level zone emphasis), HGZE (high gray-level zone emphasis), SZLGE (short-zone low gray-level emphasis), SZHGE (short-zone high gray-level emphasis), LZLGE (long-zone low gray-level emphasis), and LZHGE (long-zone high gray-level emphasis). However, the present invention is not limited thereto.

For each rectal tumor, 68 radiomics are extracted from the MTV, Accordingly, the 68 radiomic features are set as feature candidates in total, and each binary decision tree model 20 selects features from the 68 radiomic features as feature nodes. In addition, in an embodiment, these features may be further screened according to the predictive power in connection with the pCR, and it will be further described in the following paragraphs.

Figure 3:
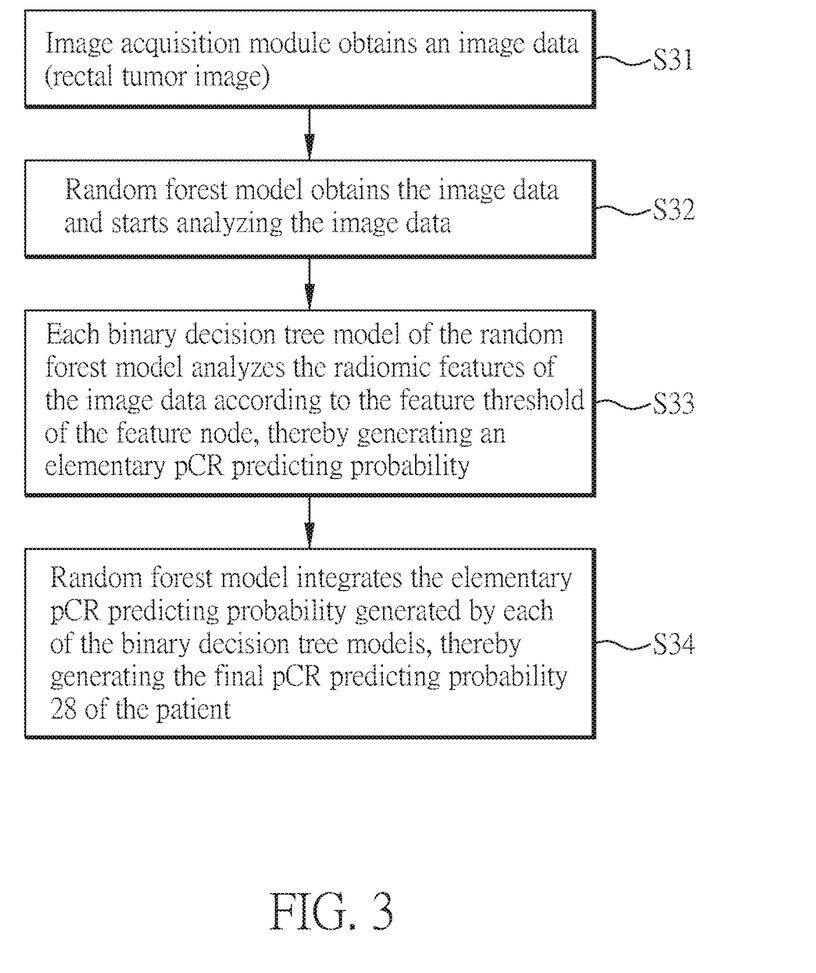
FIG. 3 is a flow chart showing the basic steps of basic steps of a computer-aided method for recognizing treatment response of rectal cancer according to an embodiment of the present invention.

The basic operation of the computer-aided recognition system for treatment response of rectal cancer 1 will be described next. FIG. 3 is a flow chart showing the basic steps of basic steps of a computer-aided method for predicting treatment response of rectal cancer according to an embodiment of the present invention, and the method is performed by the computer-aided recognition system for treatment response of rectal cancer 1 shown in FIG. 1(A) and FIG. 1(B), wherein the training for random forest model 14 is finished. As shown in FIG. 3, step S31 is first performed, the image acquisition module 12 obtains an image data (rectal tumor image) of the rectal cancer patient. Thereafter, step S32 is performed, and the random forest model 14 obtains the image data and starts analyzing the image data. Then, step S33 is performed, and each binary decision tree model 20 analyzes the radiomic features of the image data according to the feature threshold 24 of the feature node 22, thereby generating an elementary pCR predicting probability 26. Thereafter, step S34 is performed, and the random forest model 14 integrates the elementary pCR predicting probability 26 generated by each of the binary decision tree models 20, thereby generating the final pCR predicting probability 28 of the patient.

In step S31, in an embodiment, a user (for example, a physician) of the system may input the image data of the patient into the computer-aided recognition system for treatment response of rectal cancer 1 through the image acquisition module 12. In one embodiment, "image data" refers to the MTV of a PET image of a rectal tumor in the patient, which shows an abnormal metabolic response of the rectal tumor after the administration of tracer (for example, $^{18}$F-FDG). The image data may have a plurality of voxels, and the pixel value of each voxel refers to the standardized uptake value of glucose (referred as SUV hereinafter). In an embodiment, the image data may comprise 68 radiomic features, including a plurality of classical PET-related features, probability-based features, and texture features. However, the present invention is not limited thereto. In an embodiment, the radiomic features of the image data may be identified by the binary decision tree model 20 when the step S32 or S33 is performed. However, in another embodiment, said 68 radiomic features may be obtained at different time points using other methods. For instance, the 68 radiomics may be obtained in a manner of edge detector using the feature acquisition module 18, wherein the operation of the feature acquisition module 18 may be implemented by performing a computer program product 30 through the process of the system 1.

Regarding step S32 to step S33, as described in the preceding paragraphs, each binary decision tree model 20 analyzes the patient's image data (radiomic features of the rectal tumor image) and identifies the final branch and the elementary pCR predicting probability corresponding to the branch, thereby generating a plurality of elementary pCR predicting possibilities 26 for the patient.

Regarding step S34, in an embodiment, the "integration" performed by the random forest model 14 refers to summing each elementary pCR predicting probability 26 and dividing the result by the number of the binary decision tree model 20. In other words, a final pCR predicting probability 28 generated by the random forest model 14 is the average of the elementary pCR predicting probabilities 26. In another embodiment, the present invention may also employ other means to generate a final pCR predicting probability 28.

It can be seen that, after the establishment of the random forest model 14, the patient's rectal cancer PET image can be input into the computer-aided recognition system for treatment response of rectal cancer 1, and the random forest model 14 can calculate the patient's pCR predicting probability. Thereby, the medical quality of the patient can be greatly improved.

In addition, the random forest model 14 should first be established through the training of the binary decision tree model 20 to allow the random forest model 14 to perform step S31 to S34. The establishment process of the random forest model 14 will be described in detail below.

Figure 4:
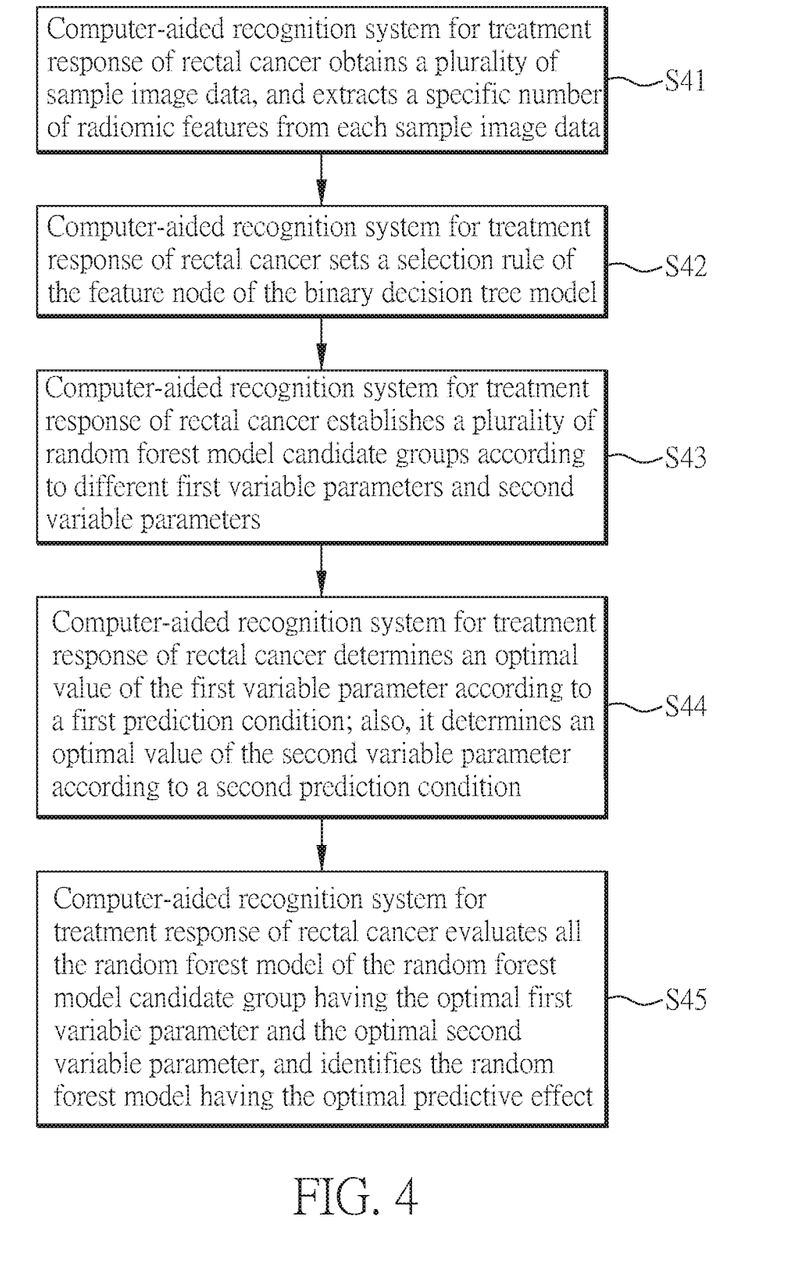
FIG. 4 is a flow chart showing the steps of a method for establishing a random forest model according to an embodiment of the present invention.

FIG. 4 is a flow chart showing the steps of a method for establishing a random forest model 14 according to an embodiment of the present invention, wherein such steps may be implemented by the instructions of the computer program product 20 performed the processor of the computer-aided recognition system for treatment response of rectal cancer 1. Please refer to FIG. 1(A) to FIG. 4. First, the step S41 is performed, the computer-aided recognition system for treatment response of rectal cancer 1 obtains a plurality of sample image data, and extracts a specific number of radiomic features from each sample image data. Thereafter, step S42 is performed, and the computer-aided recognition system for treatment response of rectal cancer 1 sets a selection rule of the feature node of the binary decision tree model 20. Then, step S43 is performed, and the computer-aided recognition system for treatment response of rectal cancer 1 establishes a plurality of random forest model candidate groups according to different first variable parameters and second variable parameters. Thereafter, step S44 is performed, and the computer-aided recognition system for treatment response of rectal cancer 1 determines an optimal value of the first variable parameter and an optimal value of the second variable parameter according to a prediction condition. Then, step S45 is performed, the computer-aided recognition system for treatment response of rectal cancer 1 evaluates all the random forest models of the random forest model candidate group having the optimal first variable parameter and the optimal second variable parameter, and identifies the random forest model having the optimal predictive effect.

Regarding step S41, this step is to identify the 68 preset feature candidates (the "preset feature candidate" may be preset in the system 1 before this step) in each sample image data by the processor of the system 1. Herein, the "sample image data" refers to the data of PET image of rectal tumors of a plurality of patients, such as MTV. Furthermore, the system 1 will know about the pCR results after NCRT for the rectal cancer patient. In an embodiment, the number of sample image data is set to 169, that is, MTV of PET images from 169 patients will be input into the computer-aided recognition system for treatment response of rectal cancer 1. However, the present invention is not limited thereto. In one embodiment, the processor of the computer-aided recognition system for treatment response of rectal cancer 1 will identify the 68 preset radiomic features from each sample image data, wherein the processor of the computer-aided recognition system for treatment response of rectal cancer 1 may identify such radiomic features in various manners, such as edge detector, histogram deviation, texture segment average distance and gray-level co-occurrence matrix (GLCM). However, the present invention is not limited thereto. In some embodiments, this step is performed when the binary decision tree model 20 establishes the feature path, alternatively.

Regarding step S42, this step is to set the selection rule of the feature node of the binary decision tree model 20 by the processor of the system 1. In an embodiment, the "selection of feature node" is set to randomly take a specific number of features from the feature candidates when each selection is made, and a feature having the optimal segmentation purity from the randomly selected features is set as a feature node. In an embodiment, the "specific number" is set to "a square root of the total number of the feature candidates, rounding up to a positive integer". If a total number of the feature candidates is 68 (sqrt(68)=9), then nine features are randomly taken out to undergo the selection when each selection is made. However, the present invention is not limited thereto.

In addition, in an embodiment, a screening step may be performed before the step S42 is performed, that is, the system 1 first screens the feature candidates to reduce the number of such feature candidates. In one embodiment, the screening step refers to a step that a processor assesses the evaluation effect of each feature candidate upon pCR through the ROC curve analysis. In one embodiment, 42 out of the 68 radiomic features are capable of differentiating tumors based on pCRs, so the number of the feature node candidates may be reduced from 68 to 42, wherein the number of classical PET-related feature, probability-based features, and texture feature is 2, 5 and 35, respectively. In another word, in this embodiment, seven radiomic features sqrt(42)=7) are randomly taken out to undergo the selection during each selection process of the feature node. The above description is only exemplary and is not a limitation of the present invention.

Regarding step S43, this step is to establish a large amount of random forest models 14 by adjusting the parameter conditions (the first variable parameter and the second variable parameter) through the processor of the system 1, wherein each parameter condition will generate the same number of random forest models 14. The plurality of random forest models 14 of each parameter condition are defined as "random forest model candidates" hereinafter. Further, for convenience of explanation, the parameter condition of the random forest model 14 is defined as RF(x1, y1), wherein x1 is the first variable parameter and y1 is the second variable parameter.

In an embodiment, the first variable parameter is preset from 1 to 10, the second variable parameter is also preset from 1 to 10, and the computer-aided recognition system for treatment response of rectal cancer 1 may establish the same number of the random forest models under parameter conditions from RF (1, 1) to RF(10, 10), respectively. In one embodiment, for each of the parameter conditions from (1, 1) to RF(10, 10), five hundred random forest model candidates are established, that is, each parameter condition corresponds to 500 random forest model candidates.

The computer-aided recognition system for treatment response of rectal cancer 1 sets the number of binary decision tree models 20 (elementary models) and the number of the feature nodes according to the parameter conditions when establishing a random forest model 14 (i.e., a random forest model candidate). The construction of the random forest by using bootstrap aggregation is achieved by individually training some decision trees and then aggregating them. To train a decision tree, a bootstrap is obtained by randomly sampling N tumors with replacement from all enrolled tumors. In an embodiment, when training an elementary model of the binary decision tree model 20, the computer-aided recognition system for treatment response of rectal cancer 1 randomly and reproducibly performs data sampling on the sample image data N times (sampling one sample image data at a time), and the sampled data is used as training data, wherein N is the number of all sample image data. For instance, if the number of all sample image data is 169 (i.e., 169 tumor images), then the system 1 randomly and reproducibly performs sampling on the 169 sample image data for 169 times. Therefore, the training data will eventually have 169 sampled data, in which some sampled data may be repeated.

When establishing a feature path of the binary decision tree model 20, for each establishment of the feature node, the system 1 randomly selects a plurality of features from the feature candidates, and then determines the actual feature and the threshold for the corresponding feature, thereby establishing the feature path. For instance, when the number of feature node candidates is 42 and the binary decision tree model 20 is set to have 10 feature nodes (the foregoing embodiment of step S42 is exemplified, presuming there are 169 training data), the system 1 randomly selects 7 features (sqrt(42)=7) from the 42 feature candidates when establishing each feature node. Furthermore, when establishing the first feature node of the binary decision tree model 20, the seven randomly selected features sequentially undergo an evaluation process to obtain the optimal threshold for each feature, wherein the optimal threshold divides the 169 training data into two groups, and the feature and threshold corresponding to the optimal segmentation result are set as the first feature node. Thereafter, assuming that 169 data, is divided into two groups of N1 and N2 data, some features are randomly selected from the N1 data, and the optimal segmentation result is identified in the aforementioned manner and set as a candidate for the second feature node. Similarly, some features are randomly selected from the N2 data, and the optimal segmentation result is identified and set as a candidate for the second feature node. Then, the segmentation results of these two candidates for the second feature node are compared, and the feature and threshold having the better segmentation result are selected and set as the second feature node. If the segmentation result of the data N1 is the second feature node and is divided into two groups of N3 and N4 data, the two candidates for the third feature node are respectively selected in the aforementioned manner. Meanwhile, the candidate for the second feature node set in the previous N2 is reset as a candidate for the third feature node, and the node having the optimal segmentation result is selected from the three candidates for the third feature node and is set as the third feature node; the similar process is performed repeatedly until 10 feature nodes are selected.

In an embodiment, the evaluation function, which is used for evaluating possible threshold of each feature, selecting the optimal segmentation threshold and comparing the optimal segmentation results of the different features according to the current data, may be an existing mathematical formula or a self-defined formula. For example, the entropy function is used for evaluation, and the function is listed below:

$$\text{Entropy} = -\Sigma p(i)\log_2 p(i),$$

wherein p(i) is the probability that whether the pCR will occur or not. For instance, assuming that there are 50 data, and pCR occurs in 20 of which, then the Entropy=$-(0.6*\log_2 0.6+0.4*\log_2 0.4)$=0.97. When a certain feature value divides the data into two groups according to a certain threshold, one group has 30 data and 15 of which have pCR, and the Entropy=$-(0.5*\log_2 0.5+0.5*\log_2 0.5)$=1; another group has 20 data and 5 of which have pCR, and the Entropy=$-(0.75*\log_7 0.75+0.25*\log_2 0.25)$=0.81. When using such feature and threshold setting, the effectiveness may be defined as $0.97-0.6*1-0.4*0.819$=0.046. However, the present invention is not limited thereto. It should be noted that the training data for each binary decision tree model 20 are selected randomly regarding each random forest model candidate, thereby generating a large number of heterogeneous feature paths.

Figure 5:
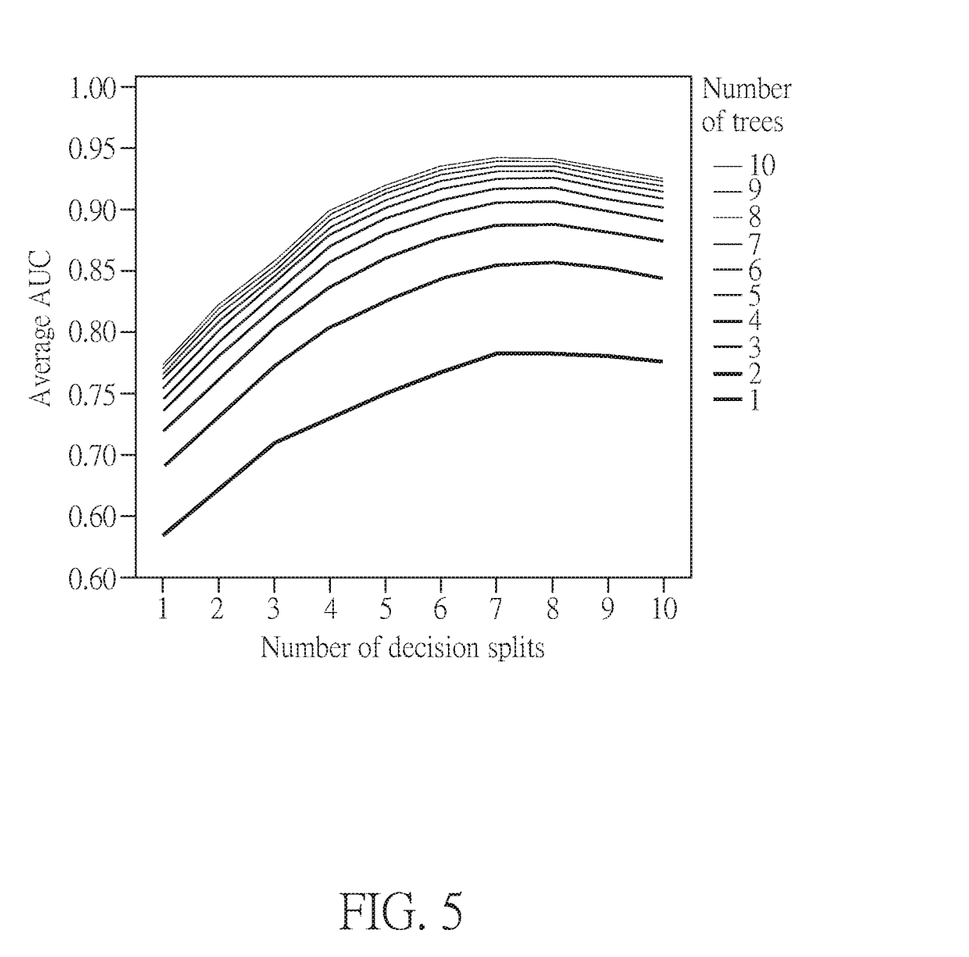
FIG. 5 is a schematic diagram showing the statistical induction of the predictive power of the random forest candidate groups according to an embodiment of the present invention.

Regarding step S44, this step is to identify, by statistical induction using the processor of the system 1, the random forest model candidate group that meets the preset condition, and the process of statistical induction may be implemented by the instruction of the computer program product 30 performed by the processor. In one embodiment, the system 1 uses all sample image data as test data. In one embodiment, the system 1 analyzes the predictive power for the pCR of each random forest candidate group through a receiver operating characteristic curve (ROC). FIG. 5 is a schematic diagram showing the statistical induction of the predictive power of the random forest candidate groups according to an embodiment of the present invention, wherein the X-axis (labeled with Number of decision splits) is the number of feature nodes in the binary decision tree model, and the Y-axis (labeled with Average AUC) is the value of area under the curve of ROC (AUC), i.e., predictive power. In addition, the lines with different thicknesses in FIG. 5 represent the number of the binary decision tree models of the random forest model candidate groups (labeled with Number of trees). As shown in FIG. 5, regarding the number of the binary decision tree model, the pCR predictive power of the random forest model group rapidly increases as the number of the binary decision tree model increases in the beginning. However, when the number of the binary decision tree model exceeds the first threshold (for example, the number is 6), the pCR predictive power of the random forest model will become moderate. In addition, regarding the number of feature nodes, the pCR predictive power of the random forest model group initially increases as the number of feature nodes of the binary decision tree model increases. However, when the number of the feature nodes exceeds the second threshold (for example, the number is 7), the pCR predictive power of the random forest model group starts to decline. Accordingly, the system 1 may set the optimal values of the first variable parameter and the second variable parameter, i.e., FR (6, 7).

In an embodiment, if the system 1 cannot identify the result that meets the preset conditions from the predictive power of the random forest model candidate group (that is, the system 1 cannot identify the declining or moderate trend of the predictive power from the result of statistical induction), it is indicated that the total number of the random forest model candidate groups is insufficient. Therefore, the system 1 will expand the preset range of the first variable parameter and the second variable parameter, for example, the maximum values of the first variable parameter and the second variable parameter may be increased from 10 to 15. However, the present invention is not limited thereto.

Regarding step S45, this step is to identify the most suitable random forest model from the random forest model group having the optimal parameters, and use said random forest model as the actually used model. In one embodiment, the system 1 conducts the screening process using a positive predictive value to identify the most suitable random forest model from the random forest model group. However, the present invention is not limited thereto.

Figure 6:
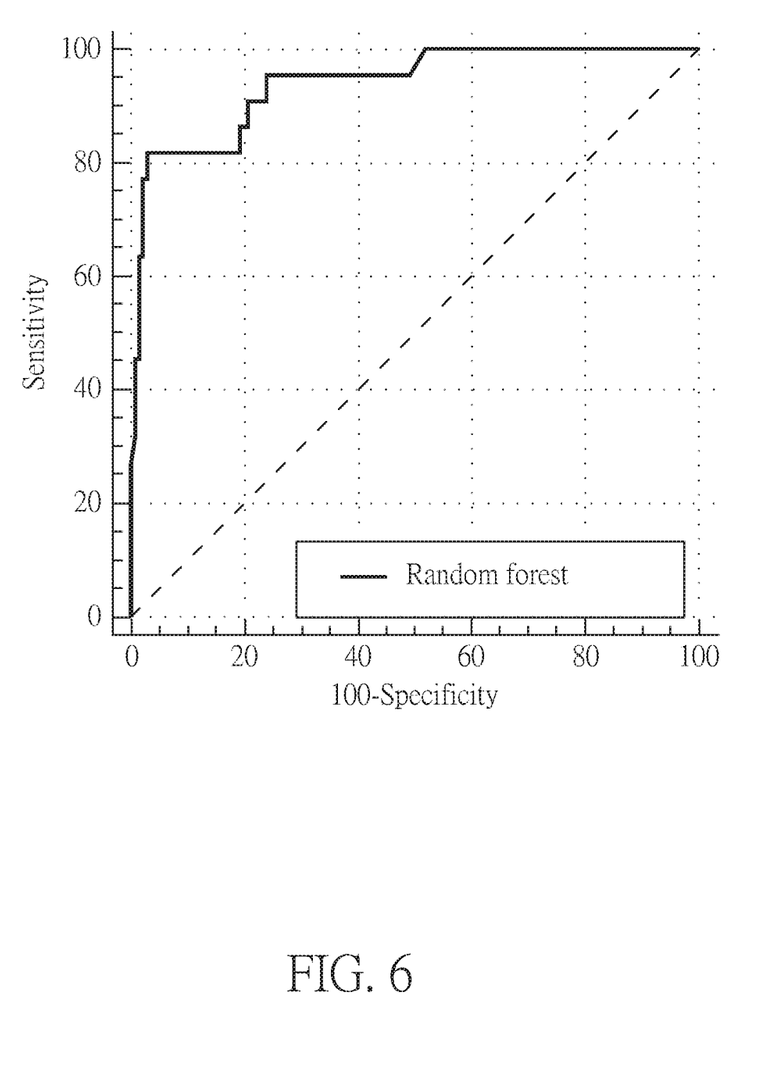
FIG. 6 is a schematic diagram showing experimental data according to an embodiment of the present invention.

FIG. 6 is a schematic diagram showing experimental data according to an embodiment of the present invention, and the diagram is a ROC curve showing the accuracy of the random forest model 14 and the conventional binary logistic regression model of the present invention for predicting the probability of pCR, wherein the Y-axis (labeled with Sensitivity) is sensitivity and the X-axis (labeled with 100-Specificity) is specificity, and both of which are tested with the same data. As shown in FIG. 6, the ROC curve (labeled with Random forest) of the random forest model 14 of the present invention has an AUC of 0.9 or more, whereas the ROC curve of the conventional binary logistic regression model (labeled with Binary logistic regression) has an AUC of 0.683. Thus, it can be seen that the random forest model 14 of the present invention has better predictive power than the conventional binary logistic regression model.

In one embodiment, the computer-aided recognition system for treatment response of rectal cancer 1, method and computer program product may be implemented by the content of "Prediction of a Pathological Complete Response in Patients with Rectal Cancer after Neoadjuvant Chemoradiotherapy through Construction of a Random Forest using Radiomics Derived from Baseline [1.8F]-Fluorodeoxyglucose Positron Emission Tomography—Computed Tomography". However, the present invention is not limited thereto.

Accordingly, the random forest model used in the present invention can be established. In other words, the random forest model can automatically predicts the pCR probability after patient receives NCRT as long as the radiomic features of the rectal tumor are input into the random forest model before the patient receives NCRT. By the random forest model configured of the binary decision tree model trained by artificial intelligence, the computer-aided recognition system for treatment response of rectal cancer can accurately predict the medical effect of the patient, assisting the patient in counseling the optimal treatment.

Although the present invention has been explained in relation to its preferred embodiment, it is to be understood that many other possible modifications and variations can be made without departing from the spirit and scope of the invention as hereinafter claimed.

What is claimed is:

1. A computer-aided recognition system for treatment response of rectal cancer for predicting the probability of a pathological complete response (pCR) in a rectal cancer patient after treatment, comprising:
   a processor; and
   a memory coupled to the processor, the memory comprising:
      an instruction, enabling a random forest model to obtain a plurality of features of a rectal tumor image of the patient, wherein the random forest model comprises at least a binary decision tree model, each binary decision tree model comprises at least a feature node corresponding to a feature threshold and each feature node has two branches, wherein each branch connects to another feature node or corresponds to an elementary pCR predicting probability;
      an instruction, enabling each binary decision tree model to analyze the plurality of features based on the at least a feature node, thereby generating the elementary pCR predicting probability of the patient;
      an instruction, enabling the random forest model to integrate the elementary pCR predicting probability generated from each binary decision tree model, thereby generating a final pCR predicting probability; and
      a plurality of instructions related to an establishment of the random forest model, the plurality of instructions related to the establishment of the random forest model comprising:
         an instruction, establishing at least 500 random forest model candidate groups according to a first variable parameter and a second variable parameter, each random forest model candidate group comprises a plurality of random forest model candidates, wherein the first variable parameter is set to the number of the binary decision tree models in the random forest model, the second variable parameter is set to the number of the feature nodes comprised in each binary decision tree model, the plurality of random forest model candidates in the same random forest model candidate group correspond to the same first variable parameter and the same second variable parameter, and different random forest model candidate groups correspond to different first variable parameters or different second variable parameters; and
         an instruction, determining an optimal value of the first variable parameter according to a first preset condition, determining an optimal value of the second variable parameter according to a second preset condition, and setting the random forest model candidate group having the optimal values as an optimal random forest model group, wherein the random forest model used to generate the elementary and final pCR predicting probabilities is selected based on the optimal random forest model group.

2. The computer-aided recognition system for treatment response of rectal cancer according to claim 1, wherein the plurality of features comprise a plurality of classical PET-related features, probability-based features and texture features.

3. The computer-aided recognition system for treatment response of rectal cancer according to claim 1, wherein the first preset condition is a situation where the first variable parameter increases while the increase of the predictive power of the random forest model candidate group slows down; and, the second preset condition is a situation where the second variable parameter increases while the predictive power of the random forest model candidate group decreases.

4. The computer-aided recognition system for treatment response of rectal cancer according to claim 1, wherein the establishment of the random forest model further comprises steps of:
   performing an assessment of predictive power on the plurality of random forest model candidates in the optimal random forest model candidate group; and
   setting the random forest model candidates having an optimal predictive power as the random forest model that is actually used.

5. A computer program product stored in a non-transitory computer readable medium for operating a computer-aided recognition system for treatment response of rectal cancer, wherein the computer-aided recognition system for treatment response of rectal cancer is used to predict a probability of achieving pathological complete response (pCR) in a rectal cancer patient after treatment, and the computer program product comprises:
   an instruction, enabling a random forest model of the computer-aided recognition system for treatment response of rectal cancer to obtain a plurality of features of a rectal tumor image of the patient, wherein the random forest model comprises at least a binary decision tree model, each binary decision tree model comprises at least a feature node corresponding to a feature threshold and each feature node has two branches, wherein each branch connects to another feature node or corresponds to an elementary pCR predicting probability;

an instruction, enabling each binary decision tree model to analyze the plurality of features based on the at least a feature node, thereby generating the elementary pCR predicting probability of the patient;

an instruction, enabling the random forest model to integrate the elementary pCR predicting probability generated from each binary decision tree model, thereby generating a final pCR predicting probability; and a plurality of instructions related to an establishment of the random forest model, wherein the plurality of instructions related to the establishment of the random forest model comprises:

an instruction, establishing at least 500 random forest model candidate groups according to a first variable parameter and a second variable parameter, each random forest model candidate group comprises a plurality of random forest model candidates, wherein the first variable parameter is set to the number of the binary decision tree models in the random forest model, the second variable parameter is set to the number of the feature nodes comprised in each binary decision tree model, the plurality of random forest model candidates in the same random forest model candidate group correspond to the same first variable parameter and the same second variable parameter, and different random forest model candidate groups correspond to different first variable parameters or different second variable parameters; and an instruction, determining an optimal value of the first variable parameter according to a first preset condition, determining an optimal value of the second variable parameter according to a second preset condition, and setting the random forest model candidate group having the optimal values as an optimal random forest model group, wherein the random forest model used to generate the elementary and final pCR predicting probabilities is selected based on the optimal random forest model group.

* * * * *